Figure 1:
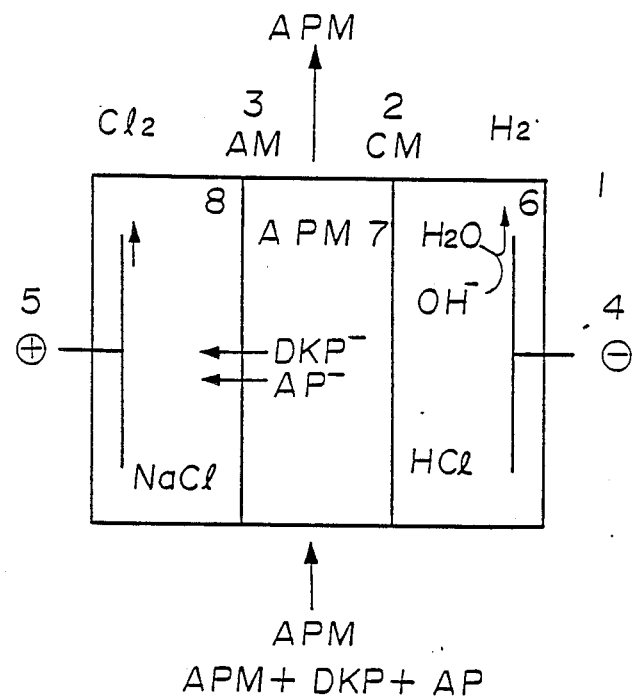

United States Patent [19]

Harada et al.

[11] Patent Number: 4,830,720
[45] Date of Patent: May 16, 1989

[54] METHOD FOR PURIFYING A DIPEPTIDE ESTER

[75] Inventors: Tsuneo Harada; Ken-ichi Fukuda; Hiroshi Shimizu; Akira Tokuda, all of Shin-nanyo; Kiyotaka Oyama, Hikari, all of Japan

[73] Assignee: Tosoh Corporation, Shin-nanyo, Japan

[21] Appl. No.: 262,600

[22] Filed: Oct. 26, 1988

[30] Foreign Application Priority Data

Oct. 26, 1987 [JP] Japan .................................. 62-268049

[51] Int. Cl.$^4$ .............................................. B01D 15/00
[52] U.S. Cl. .................................................... 204/131
[58] Field of Search ................................ 204/130, 131

[56] References Cited
U.S. PATENT DOCUMENTS 2,788,319  4/1957  Pearson ................................ 204/131

Primary Examiner—T. M. Tufariello
Attorney, Agent, or Firm—Oblon, Fisher, Spivak, McClelland & Maier

[57] ABSTRACT

A method for purifying a dipeptide ester by electrolysis in an electrolytic cell comprising an anode compartment, a cathode compartment and a central compartment partitioned by ion exchange membranes, which comprises supplying an aqueous dipeptide ester solution containing organic acids to the central compartment defined by anion and cation exchange membranes or by anion exchange membranes and an aqueous electrolyte solution to the cathode and anode compartments, and electrically removing the organic acids from the central compartment to the anode compartment through the anion exchange membrane.

6 Claims, 3 Drawing Sheets

METHOD FOR PURIFYING A DIPEPTIDE ESTER

The present invention relates to a method for purifying a dipeptide ester. More particularly, it relates to a method for obtaining α-L-aspartyl-L-phenylalanine methyl ester (hereinafter referred to simply as α-APM) by removing 3-benzyl-6-carboxymethyl-2,5-diketopiperazine (hereinafter referred to simply as DKP) and α-L-aspartyl-L-phenylalanine (hereinafter referred to simply as AP) from an aqueous solution containing DKP, AP and α-APM by an electrolytic purification method by means of anion exchange membranes.

α-APM is a dipeptide ester composed of L-aspartic acid and phenylalanine, and it is expected to be a diet sweetener.

For its production, there have been proposed a chemical peptide systhesis and a biochemical method using an enzyme or a microorganism which produces it (e.g. Kiyotaka Oyama, Bioindustry, Vol. 2, No. 9, p. 5–11, 1985).

α-APM is relatively unstable, and in either the chemical synthesis or the biochemical synthesis, DKP and AP are produced during the process for its production. As a method for separating these inclusions, it has been proposed to contact them with an anion exchange resin in an aqueous medium so that the inclusions are adsorbed on the resin and removed (Japanese Examined Patent Publication No. 4919/1975).

By a OH type ion exchange resin, α-APM will be decomposed in a substantial amount into DKP and AP by OH ions. Therefore, it is usual to employ a Cl type or acetic acid type anion exchange resin. In such a case, as the inclusions are adsorbed on the ion exchange resin, Cl or acetic acid ions formed by the ion exchange with DKP and AP in α-APM will enter into the aqueous α-APM solution.

As described in the foregoing, in either the chemical synthesis or the biochemical synthesis, an acid will be present as an impurity in α-APM when an ion exchange resin is employed.

In such a case, a step for acid removal will be required as a subsequent step in order to obtain pure α-APM. Heretofore, for such an acid removal step, it has been common to use an alkali metal hydroxide for neutralization and to obtain α-APM by crystallization. However, in this method of neutralization and crystallization, there have been problems such that α-APM is likely to be decomposed by alkali, and separated α-APM crystals include a salt formed by the neutralization.

An ion exchange resin method, an electrodialysis method or an electrolytic ion exchange method may be mentioned as an alternative method for the removal of the acid. However, each of such methods has its own problems. In the electrodialysis method, α-APM containing an inorganic acid is required to be neutralized with an alkali metal hydroxide before subjecting it to electrodialysis. Further, as the pH changes during the electrodialysis, α-APM tends to be retained in the ion exchange membrane, whereby the membrane resistance will increase. It may further happen that ionic α-APM leaks to electrode compartments, whereby the electrodes are damaged or noxious substances are produced. Further, in the dialysis by means of a porous membrane, leakage of α-APM through the membrane is substantial, thus leading to a poor yield.

In addition to the above, an electrolytic ion exchange method is known in the field of amino acid synthesis (Japanese Unexamined Patent Publication No. 55577/1983). In this process, the space between the anode and the cathode is devided by two or three hydrocarbon-type anion exchange membranes, and a hydrochloric acid solution of an amino acid is supplied to a central compartment defined by the anion exchange membranes, an aqueous solution of sodium hydroxide or potassium hydroxide is supplied to the cathode compartment and an aqueous solution of hydrochloric acid is supplied to the anode compartment, to conduct electrolytic ion exchange to obtain an amino acid solution. This process is in principle effective for the purification of an amino acid. However, there is a problem with respect to the durability of the hydrocarbon-type anion exchange membrane, since the hydrocarbon-type anion exchange membrane is usually poor in the durability against strong acid or strong alkali or under a high temperature condition. A further problem is that if the selectivity of the anion exchange membrane is inadequate, leakage of the amino acid to the cathode and anode compartments is likely to take place.

As described in the foregoing, the problems involved in the removal of the acid have not yet been adequately solved when an ion exchange resin is used for the removal of DKP and AP from an aqueous α-APM solution. Further, two steps are required i.e. one for the removal of DKP and AP and the other for the removal of the acid. Thus, there have been many technical and economical problems.

It is an object of the present invention to remove the drawbacks of the process wherein the ion exchange resin is used and to provide an economically feasible method for the purification of a dipeptide ester solution whereby the removal of DKP and AP can efficiently and simply be carried out by means of ion exchange membranes.

The present inventors have conducted extensive researches on the stability of a dipeptide ester and the leakage to the cathode compartment and anode compartment in connection with the purification of the dipeptide ester. As a result, it has been surprisingly found that according to the method of the present invention, DKP and AP permeate through an anion exchange membrane while α-APM does not substantially permeate therethrough. Namely, they have found a method for removing DKP and AP by ion electrolysis without leakage of the dipeptide ester and without decomposition of the dipeptide ester by directly supplying an aqueous dipeptide ester solution containing organic acids, particularly DKP and AP, included during the process for the production of the dipeptide ester to a central compartment of an electrolytic cell defined by anion and cation exchange membranes or by anion exchange membranes and supplying an aqueous electrolyte solution to the cathode and anode compartments. The present invention has been accomplished on the basis of this discovery.

The present invention provides a method for purifying a dipeptide ester by electrolysis in an electrolytic cell comprising an anode compartment, a cathode compartment and a central compartment partitioned by ion exchange membranes, which comprises supplying an aqueous dipeptide ester solution containing organic acids to the central compartment defined by anion and cation exchange membranes or by anion exchange membranes and an aqueous electrolyte solution to the cathode and anode compartments, and electrically removing the organic acids from the central compartment to the anode compartment through the anion exchange membrane.

Now, the present invention will be described in detail with reference to the preferred embodiments.

Figure 2:
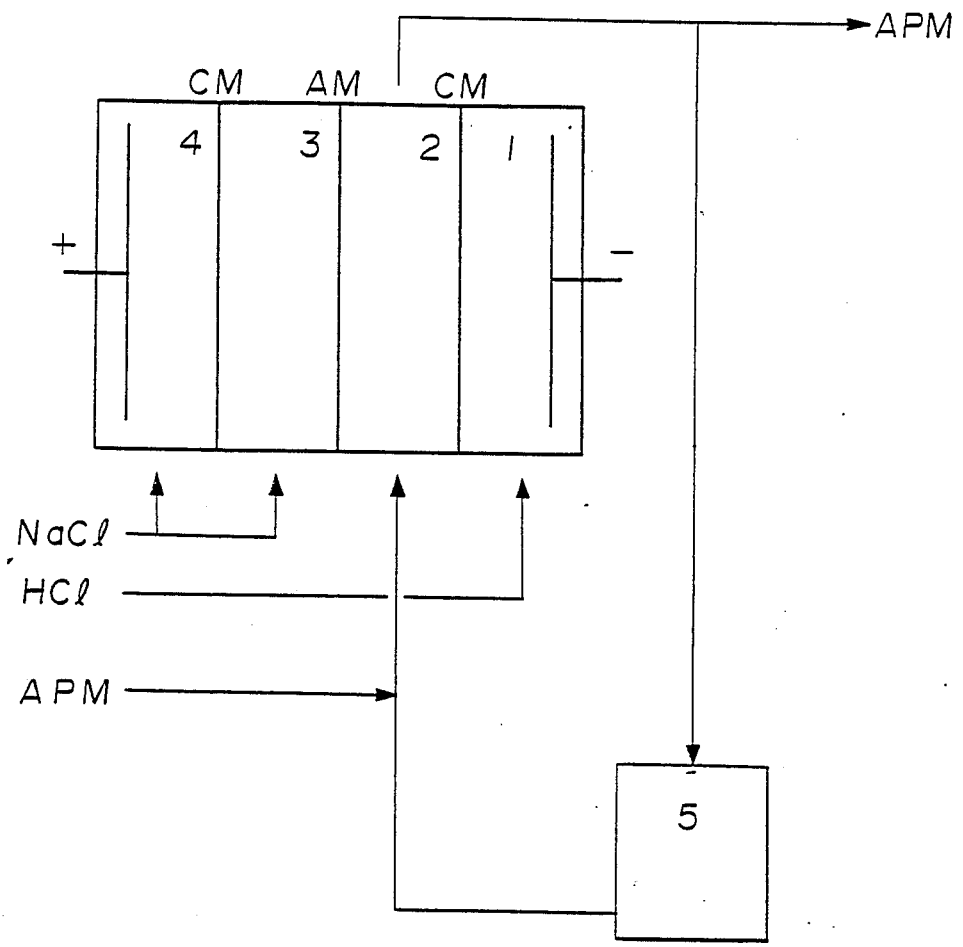
Figure 3:
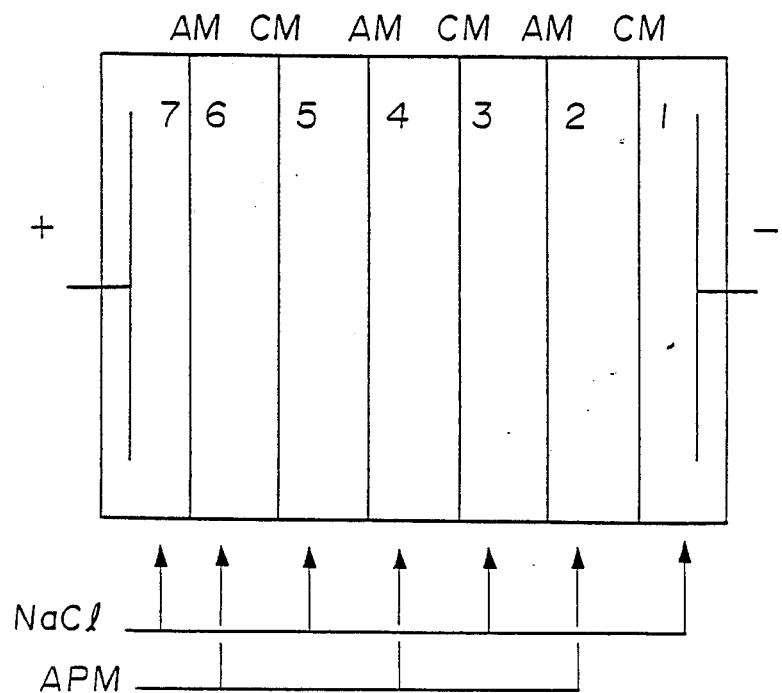

In the accompanying drawings, FIGS. 1, 2 and 3 are diagrammatical views illustrating different embodiments of the method of the present invention.

The ion species present as impurities in the dipeptide ester vary depending upon the process for the production, but they include inorganic anions such as Cl ions and $SO_4$ ions; organic anions such as DKP, AP, acetic acid and formic acid; inorganic cations such as Na ions, K ions and Ca ions, and organic cations such as phenylalanine methyl ester (PM).

In the purification of α-APM according to the method of the present invention, such inorganic and organic anions are removed to the anode compartment through an anion exchange membrane, and the inorganic and organic cations are removed to the cathode compartment through a cation exchange membrane.

FIG. 1 schematically illustrates the principle of the present invention. Namely, FIG. 1 illustrates an embodiment wherein the respective ions are removed to the cathode and anode sides by an electrolytic purification method by supplying an aqueous α-APM solution containing such ions to a three compartment-type electrolytic cell divided by two membranes of cation and anion exchange membranes. Reference numeral 1 indicates the electrolytic cell, numeral 2 indicates a cation exchange membrane (CM), numeral 3 indicates an anion exchange membrane (AM), numeral 4 indicates a cathode, numeral 5 indicates an anode, numeral 6 indicates a cathode compartment, numeral 7 indicates a central compartment, and numeral 8 indicates an anode compartment. To the central compartment 7, α-APM containing various ions is supplied. To the anode compartment 8, an aqueous sodium chloride solution is supplied, and to the cathode compartment 6, a hydrochloric acid solution is supplied.

When the electrolytic reaction is initiated, hydrogen gas is generated from the cathode 4, and chlorine gas is generated from the anode 8. From the central compartment 7, various anions are transferred to the anode compartment 8, and cations are transferred to the cathode compartment 6. Thus, the removal of inorganic ions and organic ions can be conducted by this principle.

The pH of the aqueous α-APM solution during the electrolytic purification is from 3.5 to 7, preferably from 4 to 6.5, more preferably from 4.5 to 6. If the treatment is conducted at a pH of less than 3.5, α-APM is likely to leak to the cathode side. On the other hand, if the pH exceeds 7, the decomposition of α-APM tends to be substantial, and its leakage to the anode side will increase, thus leading to a decrease of the yield of α-APM.

The solution to be supplied to the cathode and anode compartments, may be an aqueous solution of an alkali metal such as NaOH or KOH; an aqueous solution of an alkaline earth metal such as $Ca(OH)_2$ or $Mg(OH)_2$, and aqueous solution of an alkali metal or an alkaline earth metal salt such as NaCl, KCl, $CaCl_2$, $MgCl_2$, $Na_2SO_4$ or $K_2SO_4$, or an acid such as HCl, $H_2SO_4$ or $HNO_3$ or an aqueous solution thereof.

The anode and the cathode of the electrolytic cell to be used in the present invention, may be made of conventional electrode materials. To adapt them for the electrolytic process intended for the purification of α-APM, electrode materials which are inexpensive, exhibit a constant voltage and have excellent corrosion resistance, are suitably selected.

With respect to such electrode materials, for example, as the anode, an electrode obtained by coating a platinum group metal such as Pt, Ir or Rh and/or an oxide of a platinum group metal on the surface of a corrosion resistant substrate such as Ti, Ta, Zn or Nb, may be employed, and as the cathode, a metal such as Fe, Ni or Cu or an alloy thereof, or an electrode having a substance showing an overvoltage (such as Raney nickel) coated on its surface, may be employed.

In the electrolytic process intended for the purification of α-APM of the present invention, the electrolytic cell usually comprises three compartments i.e. an anode compartment, a central compartment and a cathode compartment. However, a multi-compartment type other than the three-compartment type may be selected, and it is also possible to conduct the electrolytic process with excellent efficiency by using a laminated cell.

The temperature for electrolysis may be from room temperature to 100° C., preferably from 10° to 80° C. If the temperature for electrolysis is high, the electrolytic voltage can be maintained at a low level. The solubility of α-APM in water is very small, and the solubility can be raised by raising the temperature. However, if the temperature for electrolysis is 80° C. or higher, α-APM tends to chemically change into DKP, whereby the yield of α-APM decreases.

As the ion exchange membranes, either hydrocarbon type membranes or fluorine type membranes may be used. Fluorine type membranes are preferred when used at a relatively high temperature. The type of the ion exchange groups, the ion exchange capacity and the thickness of the membrane may suitably be determined.

Now, the present invention will be described in further detail with reference to Examples. However, it should be understood that the present invention is by no means restricted to such specific Examples.

EXAMPLE 1

An electrolytic purification method was conducted to obtain pure α-APM from an aqueous solution containing 0.8% by weight of α-APM, 0.15% by weight of DKP and 0.05% by weight of AP.

The electrolytic cell was a three-compartment type electrolytic cell as shown in FIGS. 1. As the anode, an electrode having a noble metal oxide coated on a Ti expanded metal substrate was used, and as the cathode platinum was used. The electrode surface area for each of the anode and the cathode was 0.1 $dm^2$, and the distance between the anode and the cathode was 8 mm.

As an anion exchange membrane partitioning the anode compartment and the central compartment, a fluorinated anion exchange membrane (SF17, manufactured by TOSOH CORPORATION) was used, and as a cation exchange membrane partitioning the cathode compartment and the central compartment, a fluorinated cation exchange membrane (Nafion 901, trademark) was used.

To the anode compartment, a 0.5N NaCl aqueous solution was supplied. To the central compartment, an aqueous solution containing 0.70% by weight of α-APM, 0.144% by weight of DKP and 0.046% by eight of AP was supplied. To the cathode compartment, a 0.2N HCl aqueous solution was supplied and circulated.

The electrolysis was conducted at a current density of 2A/dm$^2$ at 25° C., whereby the initial electrolytic voltage was 12.5 V. As the electrolysis is continued, DKP and AP are removed to the anode compartment, and the conductivity in the circulated α-APM solution decreases. Accordingly, the electrolytic voltage increases.

When the electrolytic voltage increased to 41.5 V, the electrolysis was stopped, whereby the removal rates of DKP and AP were 97.4% and 98.1%, respectively, and the recovery rate of α-APM was 94%. Further, after the electrolysis, the amounts of α-APM in the anode compartment and the cathode compartment were measured, whereby 2.6% leakage of APM, based on the treated amount of α-APM, was detected in the anode compartment, and 1.9% leakage of APM was detected in the cathode compartment.

EXAMPLE 2

The electrolytic purification method was conducted in the same manner as in Example 1. As an anion exchange membrane partitioning the anode compartment and the central compartment, a fluorinated anion exchange membrane (R-4030, manufactured by RAIPORE Co.) was used, and as a cation exchange membrane partitioning the cathode compartment and the central compartment, a fluorinated cation exchange membrane (Nafion 901, trademark) was used. To the anode compartment, a 0.5N NaCl aqueous solution was supplied. To the central compartment, an aqueous solution containing 0.87% by weight of α-APM, 0.154% by weight of DKP and 0.050% by weight of AP was supplied. To the cathode compartment, a 0.2N HCl aqueous solution was supplied and circulated. The electrolysis was conducted at a current density of 1 A/cm$^2$ at 25° C., whereby the initial electrolytic voltage was 16 V. As the electrolysis is continued, DKP and AP are removed to the anode compartment, and the conductivity in the circulated α-APM solution decreases. Accordingly, the electrolytic voltage increases. When the electrolytic voltage increased to 41 V, the electrolysis was stopped, whereby the removal rates of DKP and AP were 70.2% and 70.3%, respectively, and the recovery rate of α-APM was 86.7%. Further, after the electrolysis, the amounts of α-APM in the anode compartment and the cathode compartment were measured, whereby 11.4% leakage of a APM was detected in the anode compartment and 3.7% leakage of APM was detected in the cathode compartment.

EXAMPLE 3

The electrolytic purification method was conducted in the same manner as in Example 1. As an anion exchange membrane partitioning the anode compartment and the central component, a fluorinated anion exchange membrane (SF17, manufactured TOSOH CORPORATION) was used, and as a cation exchange membrane partitioning the cathode compartment and the central compartment, a fluorinated cation exchange membrane (Nafion 901, trademark) was used.

To the anode compartment, a 0.5N NaCl aqueous solution was supplied. To the central compartment, an aqueous solution containing 3.41% by weight of α-APM, 0.122% by weight of DKP and 0.38% by weight of AP was supplied. To the cathode compartment, a 0.2N HCl aqueous solution was supplied and circulated.

The electrolysis was conducted at a current density of 2 A/dm$^2$ at 60° C., whereby the initial electrolytic voltages was 9.5 V.

After confirming that DKP and AP were removed, the electrolysis was stopped, whereby the removal rates of DKP and AP were 52% and 53%, respectively, and the recovery rate of APM was 91.6%. Further, the amounts of α-APM in the anode compartment and cathode compartment after the electrolysis were measured, whereby 2.7% leakage of APM was detected in the anode compartment, and 4.7% leakage of APM was detected in the cathode compartment.

EXAMPLE 4

The electrolytic cell was a four-compartment type electrolytic cell as shown in FIG. 2. As the anode, an electrode having a noble metal oxide coated on a Ti expanded metal substrate was used, and as the cathode, platinum was used. The electrode surface area for each of the anode and the cathode was 0.1 dm$^2$ and the distance between the anode and the cathode was 12 mm.

By using a fluorinated cation exchange membrane (Nafion 324, trademark) as the cation exchange membrane, the anode compartment 4 and an intermediate compartment 3 were partitioned to protect the anode from organic substances. As an anion exchange membrane partitioning the intermediate compartments 2 and 3, a fluorinated anion exchange membrane (SF17, manufactured by TOSOH CORPORATION) was used. Further, as a cation exchange membrane for partitioning the cathode compartment and the intermediate compartment 2, a flourinated cation exchange membrane (Nafion 901, trademark) was used.

To the intermediate compartment 3 and the anode compartment 4, a 0.5N NaCl aqueous solution was supplied, and to the cathode compartment, a 0.2N HCl aqueous solution was supplied and circulated. To the intermediate compartment 2, an external circulating tank 5 was provided, whereby the α-APM solution was treated in a continuous circulation system.

The supplied α-APM solution had a composition comprising 0.80% by weight of APM, 0.18% by weight of DKP and 0.049% by weight of AP.

The electrolysis was conducted at a current density of 1 A/dm$^2$ at 25° C. Continuous treatment was conducted while controlling the amount of the supply of the α-APM aqueous solution so that the electrolytic voltage was from 25 to 28 V. The average composition of the treated α-APM solution was 0.75% by weight of α-APM, 0.032% by weight of DKP and 0.0091% by weight of AP.

The removal rates of DKP and AP after completion of the electrolysis were 83% and 82%, respectively, and the recovery rate of α-APM was 92.3%. Further, the amounts of α-APM in the cathode compartment 1 and the intermediate compartment 3 were measured, whereby 2.9% leakage and 3.9% leakage of APM were detected, respectively.

EXAMPLE 5

The electrolytic purification of an α-APM solution was conducted by a multi-compartment type electrolytic cell as shown in FIG. 3. Compartments 1 and 2, compartments 3 and 4 and compartments 5 and 6 were, respectively, partitioned by cation exchange membranes (Nafion 901 trademark), and compartments 2 and 3, compartments 4 and 5 and compartments 6 and 7 were, respectively, partitioned by anion exchange membranes (SF17, manufactured by TOSOH CORPORATION). Then, a 0.5N NaCl aqueous solution was supplied to compartments 1, 3, 5 and 7, respectively, and an α-APM aqueous solution was supplied and circulated to compartments 2, 4 and 6.

The supplied α-APM aqueous solution contained 0.81% by weight of α-APM, 0.15% by weight of DKP and 0.05% by weight of AP. The electrolytic purification was conducted at 25° C. at a current density of 1 A/dm$^2$. The initial voltage was 20 V. As the electrolysis was continued, the voltage increased and when the voltage reached 65 V, the electrolysis was stopped, whereby the concentrations of various components were analyzed. The removal rates of DKP and AP were 88% and 87%, respectively, and the recovery rate of α-APM was 91%. In the circulated NaCl aqueous, 7.5% leakage of APM was detected.

The method of the present invention is particularly useful for a process of efficiently removing DKP and AP contained in the product in the production of α-APM.

According to the method of the present invention, organic acids can efficiently be removed without substantial leakage of the dipeptide ester while suppressing the decomposition of the dipeptide ester, whereby the purification of the dipeptide ester can be conducted in an extremely economical manner as compared with the conventional process.

We claim:

1. A method for purifying a dipeptide ester by electrolysis in an electrolytic cell comprising an anode compartment, a cathode compartment and a central compartment partitioned by ion exchange membranes, which comprises supplying an aqueous dipeptide ester solution containing organic acids to the central compartment defined by anion and cation exchange membranes or by anion exchange membranes and an aqueous electrolyte solution to the cathode and anode compartments, and electrically removing the organic acids from the central compartment to the anode compartment through the anion exchange membrane.

2. The method according to claim 1, wherein the dipeptide ester is α-L-aspartyl-L-phenylalanine methyl ester.

3. The method according to claim 1, wherein the organic acids are 1,3-benzyl-6-carboxymethyl-2,5-diketopiperazine and α-L-aspartyl-L-phenylalanine.

4. The method according to claim 1, wherein the electrolytic cell is partitioned into at least three compartments by anion and cation exchnge membranes or by anion exchange membranes.

5. The method according to claim 1, wherein the temperature for electrolysis is within a range of from 10° to 80° C.

6. The method according to claim 1, wherein the pH of the aqueous dipeptide ester solution is from 3.5 to 7.0.

* * * * *